United States Patent
Wohltjen

(10) Patent No.: US 8,349,260 B2
(45) Date of Patent: Jan. 8, 2013

(54) SYSTEM AND METHOD FOR LIMITING SENSOR EXPOSURE TO OZONE

(75) Inventor: Henry Wohltjen, Bowling Green, KY (US)

(73) Assignee: Microsensor Systems, Inc., Bowling Green, KY (US)

(*) Notice: Subject to any disclaimer, the term of this patent is extended or adjusted under 35 U.S.C. 154(b) by 1451 days.

(21) Appl. No.: 11/474,532

(22) Filed: Jun. 26, 2006

(65) Prior Publication Data

US 2007/0269346 A1 Nov. 22, 2007

Related U.S. Application Data

(60) Provisional application No. 60/801,966, filed on May 19, 2006.

(51) Int. Cl.
| | |
|---|---|
| G01N 7/00 | (2006.01) |
| G01N 21/00 | (2006.01) |
| G01N 27/00 | (2006.01) |
| G01N 31/00 | (2006.01) |
| G01N 33/00 | (2006.01) |
| G01N 9/00 | (2006.01) |
| G01N 19/10 | (2006.01) |
| G01N 25/00 | (2006.01) |
| G01N 29/02 | (2006.01) |
| G01N 33/497 | (2006.01) |

(52) U.S. Cl. ............................... 422/83; 73/23.2
(58) Field of Classification Search ............. 422/83
See application file for complete search history.

(56) References Cited

U.S. PATENT DOCUMENTS

| | | | |
|---|---|---|---|
| 3,652,227 A | 3/1972 | Harman et al. | |
| 3,719,457 A * | 3/1973 | Nagamatsu | 422/176 |
| 6,044,689 A | 4/2000 | Yoshida et al. | |
| 6,569,393 B1 | 5/2003 | Hoke et al. | |
| 7,140,232 B2 * | 11/2006 | Wright et al. | 73/25.01 |
| 2004/0112117 A1 | 6/2004 | Wright et al. | |
| 2005/0090018 A1 | 4/2005 | Walte et al. | |

FOREIGN PATENT DOCUMENTS

| | | |
|---|---|---|
| GB | 1249403 | 10/1971 |
| GB | 2 158 731 | 11/1985 |

OTHER PUBLICATIONS

Sample Prep Note (SPN) 2, "New Device Removes Ozone from Air Samples", Waters Corporation, www.waters.com/dww-wrootwaterswebsite/sprep.htm, Jul. 19, 1995.
"PAMSGram", "The Use of KI-Coated Copper Ozone Denuders for Carbonyl Measurement at PAMS", Oct. 13, 1998.
Hoke, J.B. et al., "PremAir® Catalyst System-Technology Update", Presented at the 93rd Annual Conference and Exhibition of the Air and Waste Management Association (A&WMA), Salt Lake City, UT, Jun. 18-23, 2000.
Greger, L. et al., "PremAire Catalyst System", SAE Technical Paper 982728, International Fall Fuels and Lubricants Meeting and Exposition, San Francisco, CA, Oct. 19-22, 1998.
Parmar, S.S. et al., "A Study of the Suitability of KI Denuders for O3 Removal During Carbonyl Measurements", presented at the Air and Waste Management Association sponsored Measurement of Toxic and Related Air Pollutants Conference, Cary, NC, Sep. 1-3, 1998.

* cited by examiner

*Primary Examiner* — Jill Warden
*Assistant Examiner* — Bryan Kilpatrick
(74) *Attorney, Agent, or Firm* — Lucas & Mercanti, LLP

(57) ABSTRACT

This invention relates to a system for mitigating the deleterious effect on a gas-detection sensor of exposure to ozone, which system comprises a sensor capable of detecting one or more select gas species, the performance of which sensor is degraded by contact with ozone, and a scrubber capable of absorbing ozone or otherwise converting ozone to one or more other substances so as to mitigate degradation of the sensor's performance; and a method for mitigating such deleterious effect as well.

16 Claims, 4 Drawing Sheets

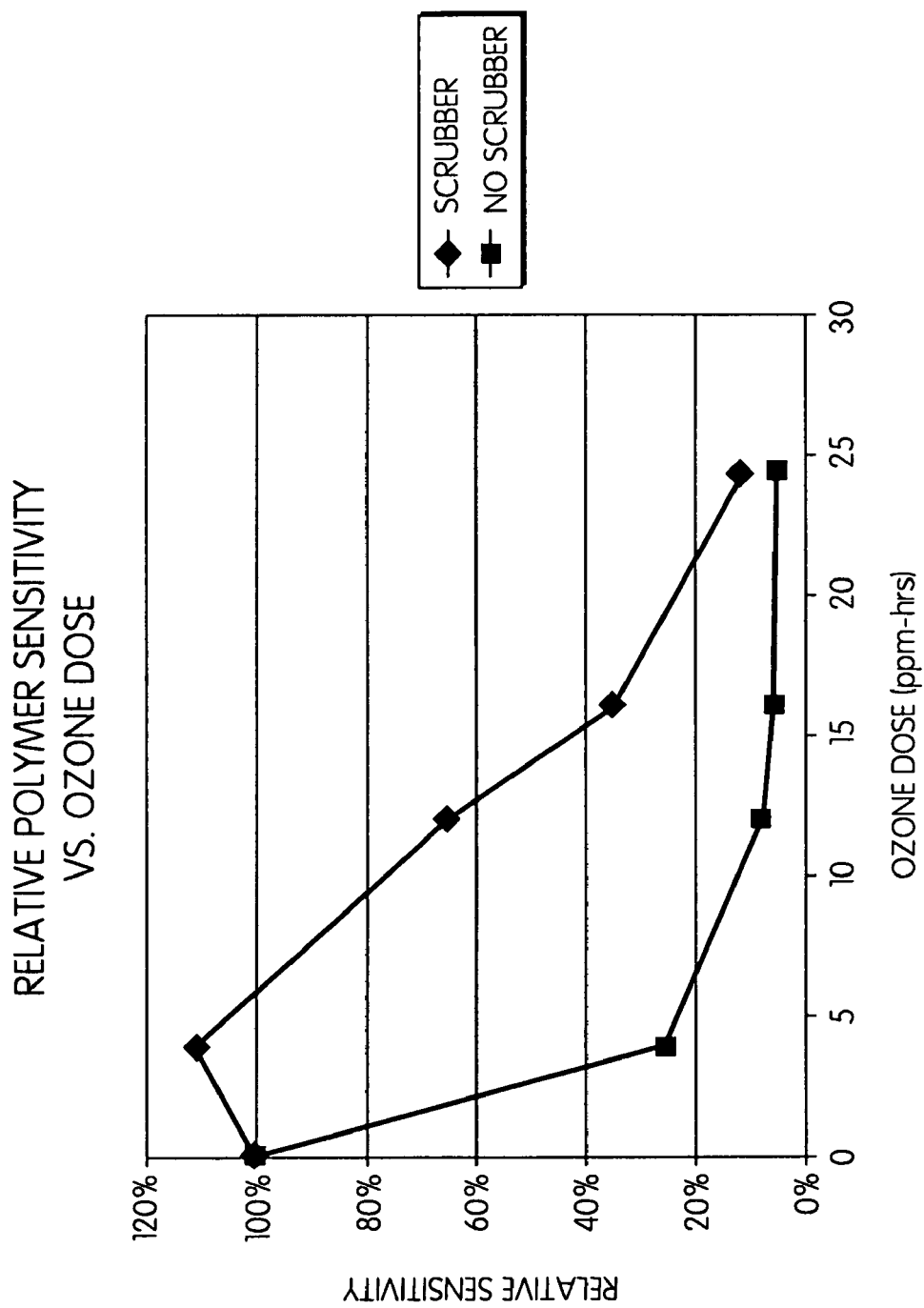

SYSTEM AND METHOD FOR LIMITING SENSOR EXPOSURE TO OZONE

This application claims the benefit of U.S. provisional application No. 60/801,966, filed May 19, 2006.

FIELD OF THE INVENTION

The present invention relates to technology for mitigating sensor performance degradation, including sensor lifetime shortening, by limiting exposure of the sensor to ozone.

BACKGROUND OF THE INVENTION

Detection devices and monitoring and measurement instruments are frequently used for ascertaining the presence and/or concentration of selected gaseous chemical species in subject environments. In addition to the selected gas species of interest, these environments may contain reactive and/or corrosive chemical materials (typically gases and vapors), the exposure of a detection sensor to which will, over a period of time, result in a degradation of the performance of the sensor, and eventually its effective inoperability.

Over and above real-time degradation in sensor performance, there are other negative consequences. For instance, the sensor performance degradation can also be manifest in the shortening of the operational lifetime of chemical sensors. Thus, their ability to serve in long-term environmental monitoring applications is compromised, thereby resulting in increased operational costs and/or the disruption of replacing the sensor more frequently than otherwise would be necessary.

Because of the obstacles to long-term monitoring, detection, and measurement that are presented by harmful chemical vapors, the identification of such harmful species, the ascertainment of the mechanism by which these species attack sensor performance, and the provision of mitigating measures would be a significant advance. More specifically, prolongation of an acceptably high level of performance and extension of the lifetime of chemical sensors, despite the presence of contaminating species, would result in reduced life-cycle costs for the user and reduced warranty exposure to the manufacturer of these devices.

It would be desirable therefore to provide a system and method for achieving more robust chemical sensor operation and for mitigating performance degradation of a sensor by a contaminant in the target environment, should such contaminant be present, while maintaining conditions that would result in a concentration of a target analyte suitable for detection by the sensor device, in the event the analyte is present.

It would also be desirable to provide an apparatus for reducing the contaminating potential of a gas sample collected from a target environment before presentation of the gas sample to a chemical sensor device suitable for long-term use without maintenance and with minimal power consumption.

SUMMARY OF THE INVENTION

The present invention solves a problem afflicting certain sensors, especially those designed for operation over extended periods of time, by identifying a harmful chemical species commonly found in gas samples and providing a system and method for reducing its concentration before the samples are presented to a sensor. More specifically, this invention involves the recognition that ozone ($O_3$), a common chemical component of atmospheric air, can have a deleterious effect on such sensors, in that it can inflict substantial damage (often rapid and irreversible) on chemical sensor performance. The present invention provides a solution whereby ozone that may be present can be converted to a less harmful substance or substances upstream from the chemical sensor. By reducing the amount of ozone that comes in contact with the sensor, a significant reduction in sensor performance degradation (optionally, including sensor lifetime shortening) can be achieved.

In one aspect, the present invention is a gas-detection system, which comprises a sensor capable of detecting one or more select gas species, the performance of which sensor is degraded by contact with ozone; and a scrubber capable of converting ozone to one or more other substances so as to mitigate degradation of the sensor's performance, the scrubber being positioned along a pathway leading to the sensor such that the scrubber and fluid in gas form traveling the pathway in the direction of the sensor can come into contact, but fluid travel via the pathway is not substantially obstructed.

In another aspect, the present invention is a gas-detection system comprising a sensor capable of detecting one or more select gas species the performance of which sensor is degraded by contact with ozone; a gaseous-fluid-inlet; a scrubber interposed between the sensor and the inlet, the scrubber being positioned along a pathway leading from the inlet to the sensor, the scrubber comprising a catalyst capable of converting ozone to one or more other substances so as to mitigate degradation of the performance of the sensor, and further comprising a substrate on a surface of which the catalyst is deposited for contact with fluid in gas form traveling the pathway.

In still another aspect, the present invention is a method for mitigating the deleterious effect of ozone on the performance of a gas-detection sensor, comprising the steps of interposing between a sensor capable of detecting one of more select gas species, the performance of which sensor is degraded by contact with ozone, and a source for fluid in gas form, which fluid may contain the one or more species and ozone, a scrubber capable of absorbing ozone or converting ozone to one or more other substances so as to mitigate degradation of the sensor's performance; and contacting the scrubber with at least a part of said fluid as it flows from said inlet toward said sensor, such that ozone which may be contained therein can be removed and contacting the sensor with throughput from the scrubber's contact with said at least part of the fluid.

For purposes of this disclosure, and throughout the same: the term "convert" (and any derivative or variation thereof) shall refer to a chemical reaction in a "scrubber" according to the invention, between ozone and another species, whereby oxygen atoms of ozone are recombined with other oxygen atoms or with atoms of at least one other element to form one or more different chemical species—generally, oxygen ($O_2$)—that is less harmful to the operation of the sensor or which are not transported from the scrubber to a "downstream" sensor under conditions of operation in accordance with the invention; the term "scrubber" will refer to any device that reduces the concentration of a particular vapor or gaseous species using an absorptive, catalytic or other chemical process; the term "mitigate" (and any derivative or variation thereof) shall mean causing to become less harsh, hostile, severe or otherwise adverse; the term "removal" (and any derivative or variation thereof) shall refer to reduction by any chemical mechanism (whether catalytic or otherwise involving a chemical reaction) of the concentration of ozone by converting it to a different chemical species; and, as applied to a scrubber, and fluid to be interacted therewith, the term "contacting" (and any derivative or variation thereof) shall refer to the provision of conditions conducive to effecting sufficient proximity between fluid material and the scrubber that chemical conversion or absorption of ozone in the fluid material can occur.

Practice of the present invention results in substantial advantages. The present invention is useful for providing a system and method for reducing the concentration of ozone to which a sensor is exposed per unit time when the target environment being monitored through use of the detection sensor contains ozone. In this manner, sensor life and performance level are prolonged. In addition, the invention is capable of affording this advantage while the concentration of gas analyte(s)—if any are present—is not counterproductively diminished. Practice of the present invention is furthermore economical in that the lifetime of the sensing device is prolonged through a reduction (or slowing) of the long-term effects of ozone on the performance of the sensor device, thus extending sensor life and reducing the disruption and cost attendant upon sensor element replacement. The necessary maintenance requirements of the sensor device are thus reduced, resulting in savings in labor and equipment costs.

BRIEF DESCRIPTION OF THE DRAWINGS

FIG. 4 is a chart showing sensor sensitivity versus ozone dose of an embodiment according to the present invention.

DESCRIPTION OF CERTAIN PREFERRED EMBODIMENTS

As indicated above, a major advantage of the present invention is the reduction in exposure of the sensor to ozone and the prolongation of an acceptably high level of sensor performance and of sensor lifetime achieved as a consequence. Reduction of contact with ozone and mitigation of its deleterious effect are particularly important to a newer generation of planar, thin-film, microelectronic sensor devices (e.g., surface acoustic wave (SAW) devices, chemiresistors, and optical waveguide devices) that typically include very thin polymer films as part of the transduction mechanism. Movement of fluid in gaseous form past the sensor, and also past the "upstream" scrubber, can be implemented in any suitable conventional manner; passive diffusion and flow induced by the action of a pump are two common ways of achieving such fluid movement. The discovery that certain sensors (such as those mentioned above) are particularly susceptible to ozone attack, a recognition of the substantial vulnerability of their performance to ozone degradation in extended real-world environments, and a solution linked to the foregoing are disclosed herein, have not to the inventor's knowledge heretofore been achieved by those practicing in the art.

Mitigation of the deleterious effect of ozone is accomplished in accordance with the present invention through ozone-removal measures (as discussed in more detail hereinafter), which, via one or more alternative approaches, reduce the concentration of ozone in the sample that comes into contact with the sensor. It will be appreciated that the mechanism by which ozone is removed can be selected from among several choices, based on the sensor's application and the corresponding degree of ozone removal required or desired. The present invention affords its practitioner a simple, reliable, and heretofore unrecognized system and method for enhancing the reliability of critical sensor technologies and represents a significant advance in the art.

The present invention will be further explained and described in the following discussion of various more specific embodiments as depicted in the accompanying drawings.

Figure 1:
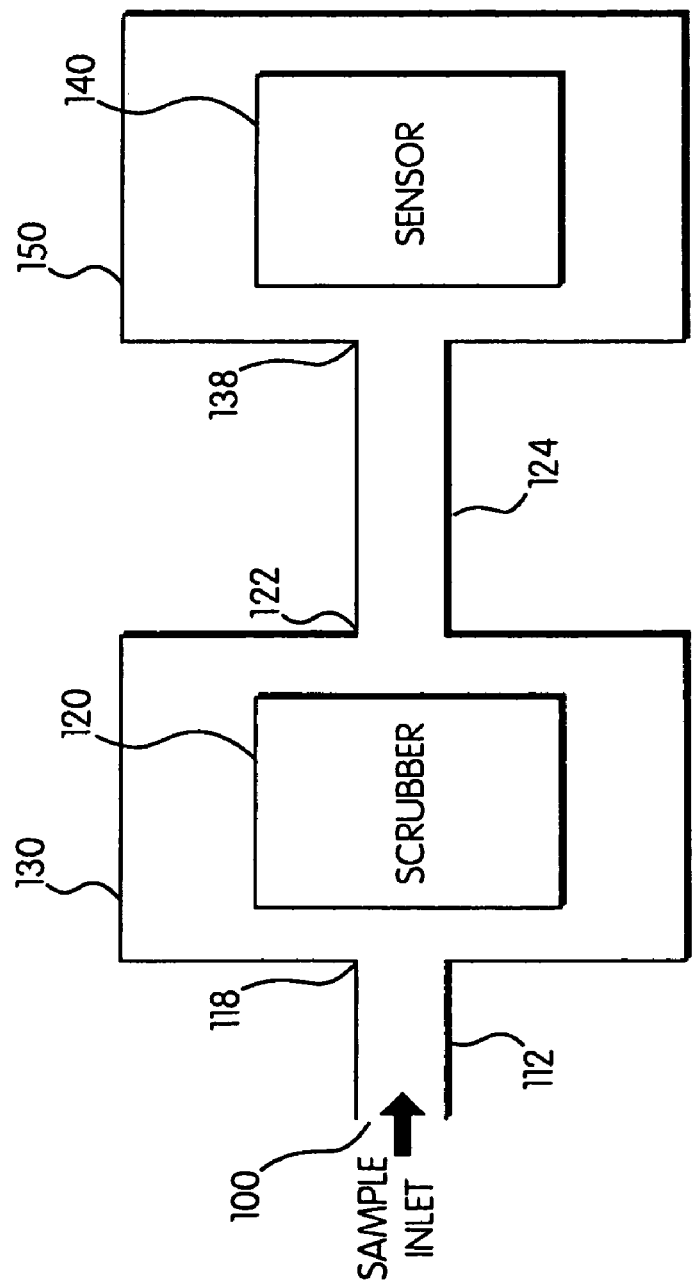
FIG. 1 is a schematic diagram showing an embodiment according to the present invention suitable for reducing ozone concentration, and thereby mitigating sensor performance degradation (e.g., extending sensor lifetime).

In accordance with FIG. 1, a preferred embodiment of the present invention comprises a sample inlet 100, a scrubber 120, and a sensor 140. More specifically, scrubber 120 is, via port 118, in communication with conduit 112, which in turn is in communication with the target environment via sample inlet 100. Scrubber 120 is also in communication via port 122 with conduit 124, which further is in communication with sensor 140 via port 138.

The embodiment shown in FIG. 1 relies on passive diffusion for transport of the gas sample through the device. A gas sample enters the system through sample inlet 100 and passes through conduit 112 into a zone defined by housing 130, which encloses scrubber 120. During its passage through the zone in which scrubber 120 resides, a desired amount of the ozone is removed from the gas sample, after which the gas material remaining enters conduit 124 and passes on to a zone defined by housing 150, which encloses sensor 140. At sensor 140, at least some of the gas sample comes into contact with the sensor element and measurement of the target analyte is obtained. After contact with sensor 140, the gas sample, through the same passive diffusion process, passes back through conduit 124 and housing 130, thereafter exiting through conduit 112 and sample inlet 100.

As previously mentioned, the process by which ozone is removed from the sample gas can be accomplished in several ways. One method involves the use of chemicals that react with ozone, thereby converting it and in some good embodiments fixing the oxygen atoms in one or more newly created reaction products such that the ozone is in a manner of speaking "absorbed." A typical ozone "absorbing" chemical, or "denuder," is potassium iodide (KI), which reacts with ozone and water vapor to form iodine, oxygen and potassium hydroxide:

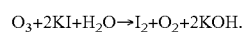

$$O_3 + 2KI + H_2O \rightarrow I_2 + O_2 + 2KOH.$$

Potassium iodide denuders are often used in environmental analysis methods to eliminate ozone interference from quantitative measurements of atmospheric carbonyl compounds and can be utilized in practicing the present invention. Another chemical material known to be reactive with ozone is poly(isoprene), which can also be used in accordance with the present invention. Other materials that react with ozone to sequester it or convert it to less detrimental substances include activated carbon and polyphenylene sulfide wool.

While utilization of such substances is advantageous in contrast to proceeding without ozone-protection, there is the shortcoming that ozone absorbing chemicals, as components in the reaction or interaction with ozone, are consumed. As a result, these ozone absorbing chemicals will be depleted over time and will have to be replaced at appropriate intervals to ensure continued effectiveness of the system.

A more attractive approach for ozone-conversion is to use a catalyst. In addition to a capability for rapidly converting ozone into oxygen, ozone catalysts confer the additional advantage that they are not consumed by the conversion process. Upon contact with the ozone catalyst, the highly reactive ozone in an ambient gas sample will be rapidly converted into the far less reactive oxygen, thereby mitigating the deleterious effects of ozone exposure on sensor materials that come into subsequent contact with the gas sample.

The widely known PremAirg ozone catalyst, which is manufactured by the Englehard Corporation and comprises a proprietary manganese oxide formulation that can be deposited as a thin coating onto surfaces, is one such catalyst suitable for use in the invention. The PremAir® catalyst and other catalysts capable of effectively converting ozone into oxygen or another relatively innocuous substance can be used in accordance with the present invention. Some examples include high surface area metal oxide catalysts, such as oxides of manganese ($MnO_2$ and $Mn_2O_3$), copper (CuO), aluminum ($Al_2O_3$), and zirconium ($ZnO_2$), and/or combinations thereof, and metallic silver on high surface area copper.

While ozone catalysts are not consumed in catalytic conversion, their lifetimes are not unlimited, as they suffer from "deactivation" effects common to catalysts. Generally, "deactivation" of the catalyst occurs when the catalyst comes into contact with solid or gaseous contaminants, resulting in masking, poisoning, and/or fouling of the catalyst. As a result, over time, the effects of these processes may result in a reduction in the conversion efficiency of the catalyst.

While the embodiment illustrated in FIG. 1 relies upon a passive diffusion process to bring the gaseous sample to the sensor for analysis, other methods can be used to transport the gaseous sample to the sensor. For example, the embodiment shown in FIG. 2 utilizes a pump to pull the gaseous sample to the sensor for analysis.

Figure 2:
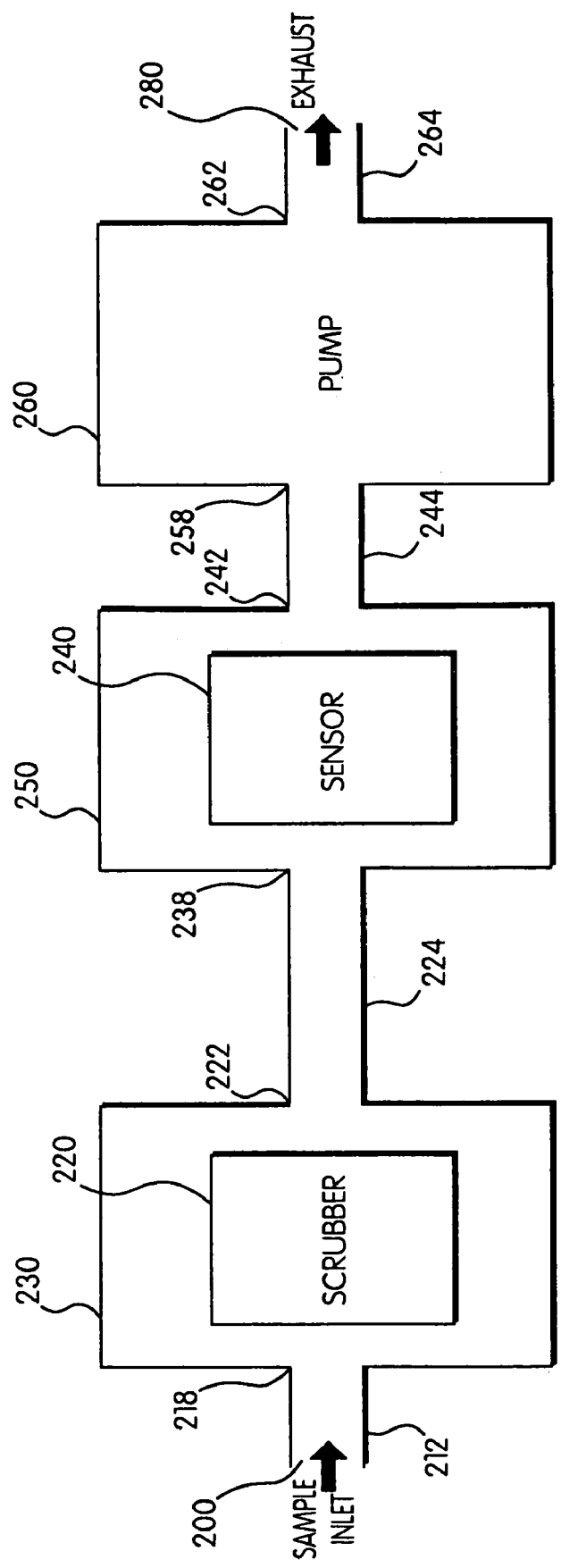
FIG. 2 is a schematic diagram showing another embodiment according to the present invention suitable for reducing ozone concentration, and thereby mitigating sensor performance degradation (e.g., extending sensor lifetime), including a pump.

Thus, as shown in FIG. 2, the present invention comprises a sample inlet 200, a scrubber 220, a sensor 240, a pump 260, and an exhaust 280. More specifically, scrubber 220 is in communication via port 218 with conduit 212, which in turn is in communication with the target environment via sample inlet 200. Scrubber 220 is also in communication via port 222 with conduit 224, which is also in communication with sensor 240 via port 238. Sensor 240 is in communication via port 242 with conduit 244, which further is in communication with pump 260 via port 258. Pump 260, via port 262, is in communication with conduit 264, which is in communication with exhaust 280.

Through the action of pump 260, a gas sample is drawn through sample inlet 200 and through conduit 212 into a zone defined by housing 230 which encloses scrubber 220, wherein an amount of ozone, if present, is removed from the gas sample. The gas material remaining is then drawn through conduit 224 and into housing 250 enclosing sensor 240, wherein at least some of the gas material is contacted with the sensor and the appropriate target analyte measurement obtained. The gas sample is then drawn through conduit 244 by and through pump 260, after which it is passed through conduit 264 and exhausted through exhaust 280.

The use of a pump to draw the gas sample through zones wherein the scrubber and sensor, respectively, are located offers several advantages over passive diffusion. First, it promotes consistency in operation of the system. As will be discussed later in detail, by setting up a substantially constant flow rate by or through the scrubber, an accurate ozone conversion rate can be determined. Second, use of the pump ensures that fresh gas samples are being drawn into the system for analysis at the desired intervals for measurement. However, as a power source is required to operate the pump, the practitioner of pump-driven embodiments must accept an increase in power consumption.

The pump can be operated on a constant basis, or operated intermittently (preferably at predetermined intervals for predetermined durations), depending on the need for constant measurement or, alternatively, measurement at intervals. Intermittent operation offers several advantages. For example, as the pump is not operating continuously, its power requirements are less than that of a pump in continuous operation. Also, during periods in which the pump is not in operation, there is a hiatus in the introduction of new samples from the target environment that possibly could contain ozone, thereby reducing the sensor's exposure to ozone.

Figure 3B:
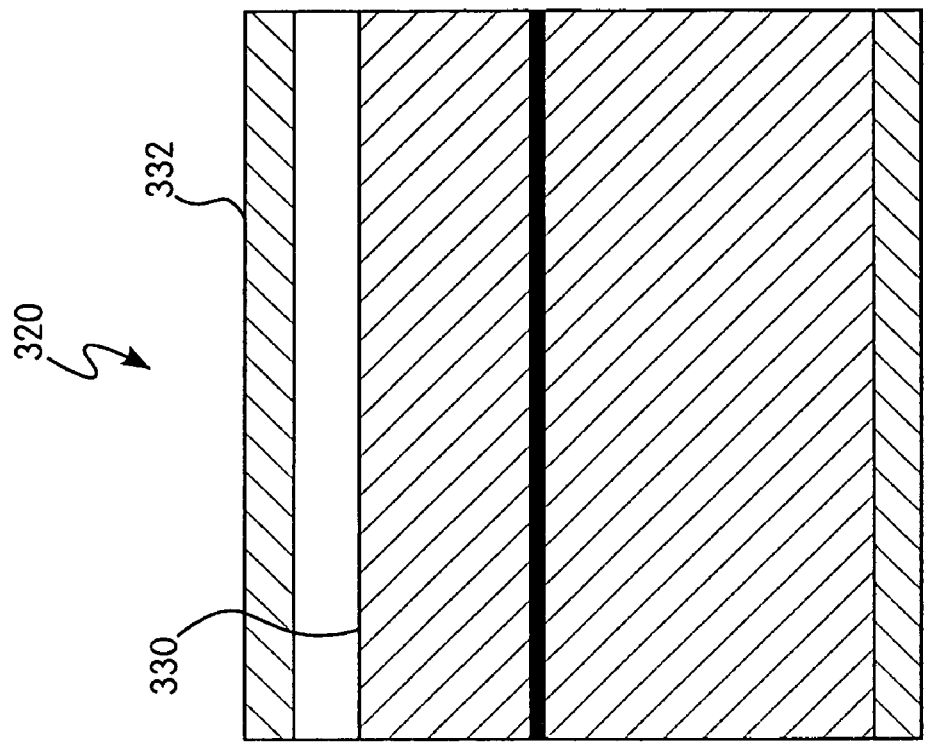
FIG. 3B is a schematic diagram of a side view of the device shown in FIG. 3A.
Figure 3A:
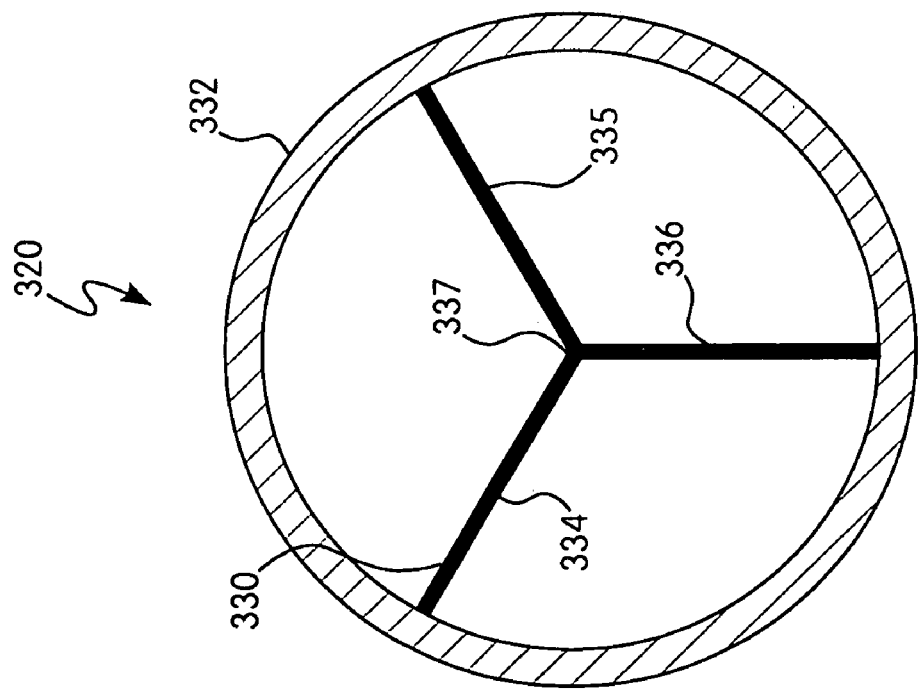
FIG. 3A is a schematic diagram of an end view of an embodiment according to the present invention of a device suitable for reducing ozone concentration, and thereby mitigating sensor performance degradation (e.g., extending sensor lifetime).

The design of the scrubber can be varied to suit the particular application of the system. One embodiment of the scrubber is shown in FIGS. 3A and 3B, in both an end view and side view, respectively. Scrubber 320 comprises cylindrical tube 332 and "Y"-shaped insert 330. In this embodiment, cylindrical tube 332 has an internal diameter of 0.45 cm and a length of 1.0 cm. As shown in FIG. 3A, "Y"-shaped insert 330 consists of rectangular members 334, 335, and 336, preferably constructed of metal, joined at common longitudinal axis 337, with insert 330 being oriented such that longitudinal axis 337 is substantially parallel with the longitudinal axis of cylindrical tube 332. Of course, inserts of other shapes can be utilized as substrates for the catalyst, such as an "X"-shaped member or various other configurations presenting at least one surface for catalyst deposition. In each case, the insert is oriented so that fluid flow past it is substantially unobstructed (for purposes of this disclosure, and throughout the same, the term "substantially unobstructed" shall mean that flow towards the sensor is not so disrupted that the reliability of determining the presence, or quantity (if a quantitative analysis is desired), of the target analyte(s) is compromised).

The volume of the scrubber shown in FIGS. 3A and 3B, as a cylindrical tube having an interior diameter of 0.45 cm and a length of 1.0 cm, will be 0.16 $cm^3$ (or $\Pi*(0.45\ cm/2)^2*1.0$ cm). Data provided by the manufacturer indicates that the PremAir® catalyst maintains an ozone conversion rate of greater than 85% at space velocities below 100,000 per hour. The space velocity is equal to the number of times per hour that a spatial volume is replenished by the gas flowing through that volume. In the context of the present invention, the space velocity of interest is that of the volume defined by the scrubber, or "cell," featuring the catalyst-coated surfaces (e.g., in FIG. 3, the volume defined by cylindrical tube 332). In the case of an embodiment utilizing a pump to pull the gaseous sample through the system, subjecting the volume to a flow rate of about 200 $cm^3$/min (or 12,000 $cm^3$/hour) will result in an anticipated space velocity of about 75,000/hour, which according to the manufacturer falls within the region of very high conversion efficiency (greater than 85%) for the PremAir® catalyst. For embodiments in which passive diffusion is utilized to transport the sample to the sensor, the flow rates can be expected to be much lower, and thus the conversion efficiency much higher.

Provided that both sides of the rectangular members 334, 335, and 336 comprising the "Y"-shaped insert 332 are coated with the catalyst, the total area of the catalyst coated insert will be as follows:

$$A_c = 3 \times L \times D$$

where $A_c$=the total area of the metal insert covered with catalyst (cm$^2$);

L=the length of the insert (cm); and

D=the inner diameter of the tube occupied by the insert (cm).

In a configuration wherein only the insert 332 is covered by the catalyst material, a significant percentage of the surface of the scrubber will remain uncoated by catalyst (e.g., the area of the interior wall of the rectangular cylinder 330). Naturally, since not all available surface areas will be covered by the catalyst, the effectiveness of the cell in converting ozone will be less than a cell wherein all surfaces are coated, in that not all wall interactions with ozone will result in a potential conversion to oxygen. The "spatial efficiency," a measure of the percentage of available surface area covered by the catalyst, can be calculated as follows:

$$E_s = 100 A_c / (A_c + A_t)$$

where $E_s$=the spatial efficiency;

$A_c$=the total area of the metal insert covered with catalyst (cm$^2$); and $A_t$=the total surface area of the uncoated tube interior (cm$^2$).

For the configuration illustrated in FIG. 3, the spatial efficiency is expected to be approximately 49% (1.35 cm$^2$/(1.35 cm$^2$+1.41 cm$^2$)=0.49).

The combined efficiency of the scrubber can be calculated using the product of the catalyst conversion efficiency and the spatial efficiency of the scrubber. Depending upon the composition and condition of the catalyst, the catalyst conversion efficiency can vary from about 20% to over 95%. Assuming a catalyst conversion efficiency of 90%, it is expected that the combined efficiency will be 44% (0.90*0.49=0.44), and that approximately 44% of the ozone will be converted to oxygen. It is expected that a reduction in ozone exposure of this magnitude will result in an approximately 80% increase in the lifetime of the sensor.

Clearly, by increasing the percentage of the total surface area of the insert covered by the catalyst, a higher spatial efficiency, and thus a corresponding higher efficiency in the removal of ozone, can be achieved, resulting in an increase in sensor lifetime. By varying the design of the scrubber, for example, by implementing a honeycomb design in the scrubber insert, a much higher spatial efficiency can be achieved.

While the efficiency in removing ozone is an important consideration in the design of the scrubber, an equally important consideration is balancing ozone removal with the device's efficiency in removing the select gas species to be detected by the sensor, i.e., the target analyte. For instance, a configuration that is very effective in removing ozone from the gaseous sample may be equally effective at removing the target analyte, the undesirable consequence being that the system is likely to provide an inaccurately low measurement of the concentration of the target analyte in the original gas sample. Therefore, it is desirable to choose a design of the scrubber that balances ozone removal with the removal of the target analyte. Once the present invention is in the possession of those skilled in the art, the correct balance for any particular situation is a matter of empirical determination, and is within the competence and ability of an ordinarily skilled worker.

The ability to vary the spatial efficiency and thus the overall efficiency of the ozone catalysts affords advantages over "ozone absorbing" chemicals in certain applications. For example, in the detection of trace levels of chemical warfare agents, the use of potassium iodine reactive "denuders" is impracticable in that significant absorption of the target chemical warfare agent vapors occurs. For such an application, the catalytic approach with its ability to balance conversion efficiency proves to be superior.

The "Y" configuration illustrated in FIG. 3 provides a design that balances ozone removal with the removal of the target analyte, as it has been demonstrated to reduce the concentration of the target analyte vapors by only 5% to 40% depending on the selected analyte. For most applications, a degree of attenuation in that range is deemed to be acceptable.

Tests of an embodiment using the "Y" configuration shown in FIG. 3A demonstrate its ability to mitigate the effects of ozone on the sensor, as shown in FIG. 4. In this example, a surface acoustic wave (SAW) micro sensor device was coated with a thin film of a sensitizing carbosilane fluoropolymer. The sensor was then exposed to a known concentration of ozone for specific periods of time. Periodically, the sensor was disconnected from the ozone exposure apparatus and the sensitivity to a vapor containing the target analyte dimethylmethyl phosphonate (DMMP) was measured, and those measurements then normalized to the sensitivity observed at 0 ppm-hrs of ozone exposure. An identical test was then conducted with the benefit of the scrubber. These results are shown in FIG. 4, which charts the relative sensitivity of the sensor to analyte DMMP versus the system's exposure to ozone, and illustrates the effectiveness of the scrubber in reducing the degradation in the sensitivity of the carbosilane fluoropolymer. For instance, after 12 ppm-hours of ozone exposure, the unprotected sensor had degraded to a sensitivity that was less than 10% of its starting level, while the sensor with the scrubber was still providing 65% of its initial sensitivity after this same exposure.

As previously discussed, the optimal scrubber configuration for a given application can be selected based on the desired compromise between ozone concentration reduction versus sample analyte concentration reduction. For example, in certain situations in which the sensor has more than adequate sensitivity for detecting the target analyte, a tradeoff can be made to allow greater removal of both ozone and the target analyte in exchange for a greater extension of the operating life of the sensor. A similar compromise might also be desirable where the system is being used to obtain only qualitative measurements (i.e., the presence or absence of a certain analyte in an environment) and a greater reduction in the target analyte's concentration can be tolerated.

The present invention described herein is susceptible of many modifications and variations within its scope, and in particular extends to the use of any one or more of the singular and several features of the foregoing description and accompanying drawings and their equivalents.

What is claimed is:

1. A gas-detection system, comprising:
    a sensor capable of detecting one or more select gas species, the performance of which sensor is degraded by contact with ozone; and
    a scrubber capable of converting ozone to one or more other substances so as to mitigate degradation of the sensor's performance, the scrubber being positioned along a pathway leading to the sensor such that the scrubber and fluid in gas form traveling the pathway in the direction of the sensor can come into contact, but fluid travel via the pathway is not substantially obstructed, wherein the scrubber comprises a "Y"-shaped insert consisting of three rectangular members joined at a common longitudinal axis and extending along the scrubber, the insert being oriented so that the longitudinal axis is substantially parallel with the direction of the flow of the fluid and wherein said "Y"-shaped insert does not interfere with the flow of the fluid.

2. The system as described in claim 1, wherein the scrubber comprises an ozone absorbing material.

3. The system as described in claim 1, wherein the scrubber comprises a catalyst.

4. The system as described in claim 1, further comprising a pump for inducing flow of fluid in gas form possibly containing the species such that at least some of the fluid comes in contact with the sensor.

5. The system as described in claim 4, wherein the pump induces flow of the fluid to a zone proximate to the scrubber, and the flow of gaseous material from the zone to the sensor.

6. The system as described in claim 5, further comprising a gaseous-fluid-inlet at the end of the pathway opposite the end proximate the sensor and wherein the scrubber is interposed between the sensor and the inlet.

7. The system as described in claim 6, wherein the scrubber comprises an ozone absorbing material.

8. The system as described in claim 6, wherein the scrubber comprises a catalyst.

9. The system as described in claim 1, wherein the scrubber is capable of selectively converting ozone without conversion of the one or more select gas species.

10. The system as described in claim 1, wherein the scrubber is designed for converting a predetermined amount of ozone present in the fluid.

11. A gas-detection system, comprising:
a sensor capable of detecting one or more select gas species, the performance of which sensor is degraded by contact with ozone;
a gaseous-fluid-inlet;
a scrubber interposed between the sensor and the inlet, the scrubber being positioned along a pathway leading from the inlet to the sensor, the scrubber comprising a catalyst capable of converting ozone to one or more other substances so as to mitigate degradation of the performance of the sensor, and further comprising a substrate on a surface of which the catalyst is deposited for contact with fluid in gas form traveling the pathway; and
a pump for inducing flow of fluid in gaseous form to a zone proximate the scrubber, and the gaseous material from the zone to the sensor, wherein the substrate comprises a "Y"-shaped insert consisting of three rectangular members joined at a common longitudinal axis and extending along the scrubber, the insert being oriented so that the longitudinal axis is substantially parallel with the direction of the flow of the fluid and wherein said "Y"-shaped insert does not interfere with the flow of the fluid.

12. A method for mitigating the deleterious effect of ozone on the performance of a gas-detection sensor, comprising the steps of:
interposing between a sensor capable of detecting one or more select gas species, the performance of which sensor is degraded by contact with ozone, and a source for fluid in gas form, which fluid may contain the one or more species and ozone, a scrubber capable of converting ozone to one or more other substances so as to mitigate degradation of the sensor' performance; and
contacting said scrubber with at least a part of the fluid as it flows from said inlet toward said sensor, such that ozone which may be contained therein can be removed and contacting the sensor with throughput form the scrubber's contact with said at least part of the fluid, wherein said scrubber comprises a "Y"-shaped insert consisting of three rectangular members joined at a common longitudinal axis and extending along the scrubber, the insert being oriented so that the longitudinal axis is substantially parallel with the direction of flow of the fluid and wherein said "Y"-shaped insert does not interfere with the flow of the fluid.

13. The method as described in claim 12, wherein the scrubber comprises an ozone absorbing material.

14. The method as described in claim 12, wherein the scrubber comprises a catalyst.

15. The method as described in claim 12 further comprising inducing, via the action of a pump, the fluid to contact the scrubber and inducing, via the action of the pump, the throughput from the scrubber to contact the detection system.

16. The method as described in claim 12, wherein the scrubber is capable of selectively converting ozone without conversion of the one or more select gas species.

\* \* \* \* \*